US00PP11861P2

(12) United States Plant Patent
Clark et al.

(10) Patent No.: US PP11,861 P2
(45) Date of Patent: May 8, 2001

(54) BLACKBERRY PLANT NAMED 'CHICKASAW'

(75) Inventors: John Reuben Clark; James Norman Moore, both of Fayetteville, AR (US)

(73) Assignee: University of Arkansas, Fayetteville, AR (US)

( * ) Notice: Subject to any disclaimer, the term of this patent is extended or adjusted under 35 U.S.C. 154(b) by 0 days.

(21) Appl. No.: 09/228,498

(22) Filed: Jan. 11, 1999

(51) Int. Cl.[7] ..... A01H 5/00

(52) U.S. Cl. ..... Plt./203
(58) Field of Search ..... Plt./203

*Primary Examiner*—Bruce R. Campell
*Assistant Examiner*—Anne Marie Grünberg

(57) ABSTRACT

Description and specifications of a new and distinct blackberry variety which originated from seed produced by a hand pollinated cross of Arkansas Selection 842 (non-patented) and Arkansas Selection 1246 (non-patented) is provided. This new blackberry variety can be distinguished by its very large fruit size, high fruit yields, erect canes, late ripening, long harvest period, and good postharvest fruit characteristics.

3 Drawing Sheets

SUMMARY OF THE INVENTION

The new and distinct variety of blackberry originated from a hand pollinated cross of Arkansas Selection 842 (non-patented)×Arkansas Selection 1246 (non-patented) made in 1985 at the Arkansas Agricultural Experiment Station Fruit Substation at Clarksville, Ark. The parent plants used in this hybridization have not been named or released and are unavailable in commerce.

Plants and fruit of this new variety differ phenotypically from its parents. The new variety is earlier ripening and possesses larger fruit size, better fruit firmness, greater vigor, and more erect canes than the parent Arkansas Selection 842, and is later ripening and more productive than the parent Arkansas Selection 1246. The new variety retains larger fruit size throughout the harvest season than either of the parent blackberries. Although blackberries (Rubus subgenus Rubus) are highly heterogeneous and outcrossing, and most clones contain genes from more than one species, the new variety and its progenitor lines phenotypically exhibit characters predominately of the erect eastern United States species, *Rubus allegheniensis* Porter (highbush blackberry) possibly introgressed with *R. argutus* Link. (tall blackberry).

The seeds resulting from this controlled hybridization were germinated in a greenhouse in the spring of 1986 and planted in a field on the Arkansas Agricultural Experiment Station in Clarksville, Ark. The seedlings fruited during the summer of 1988 and one, designated Ark. 1647, was selected for its very large fruit size, erect plant growth habit, and good fruit quality.

During 1988, the original plant selection was propagated asexually from root cuttings, at the above noted location, and a test row of 20 plants was established. Subsequently, larger test plantings have been established with asexually multiplied plants at three additional locations in Arkansas.

The new variety has been asexually multiplied annually since 1988 by the use of root cuttings: it readily forms new plants from adventitious buds on root cuttings. During all asexual multiplication, the characteristics of the original plant have been maintained and no aberrant phenotypes have appeared.

Test plantings over a wide geographic area in Arkansas have shown this new variety to be adapted to differing soil and climatic conditions.

Plants of the new variety are vigorous and prolific and row establishment following planting is rapid. Both primocanes and floricanes are erect in growth habit but the new variety is not as rigidly erect as the 'Shawnee' (U.S. Plant Pat. No. 5,686) variety. The plants are moderately thorny, with size and density of thorns being similar to the 'Shawnee' (U.S. Plant Pat. No. 5,686) variety and less than the 'Kiowa' (U.S. Plant Pat. No. 9,861) variety. Plants and fruit are moderately tolerant to anthracnose [*Elsinoe veneta* (Burkh.) Jenkins], and plants appear immune to orange rust [(*Gymnoconia nitens* (Schwein.) F. Kern and H. W. Thurston.] The new variety blooms in the spring an average of 4 days earlier than the 'Shawnee' (U.S. Plant Pat. No. 5,686) variety.

Fruit of the new variety begins ripening 3 days later than the 'Shawnee' (U.S. Plant Pat. No. 5,686) variety, and produces ripe fruit an average of 3 days longer than the 'Shawnee' (U.S. Plant Pat. No. 5,686) variety. Average first ripening date is June 10 in central Arkansas and average last harvest is July 20. The harvest period is long, with ripening over nearly a 6 week period, in contrast to most blackberry varieties that produce for 4 to 5 weeks. Fruit yields are usually 7 to 7.5 lb/plant and are equal to or higher than the 'Shawnee' (U.S. Plant Pat. No. 5,686) variety (yields are 5 to 7 lb/plant) at all test locations and high production is more consistent across a wide geographic range than for 'Shawnee' (U.S. Plant Pat. No. 5,686). Yields are consistent from year to year.

The fruit is long, cylindrical and slightly flattened in shape, bright glossy black in color and very large in size (9–11 g). The fruit averages 20% larger than the 'Shawnee' (U.S. Plant Pat. No. 5,686) variety, and fruit size of the new variety is maintained well throughout the harvest season. The fruit is moderately firm at maturity, rating more firm than the 'Shawnee' (U.S. Plant Pat. No. 5,686) and 'Choctaw' (U.S. Plant Pat. No. 6,678) varieties, but less firm than the 'Navaho' (U.S. Plant Pat. No. 6,679) variety. Storage ability of fresh fruit of the new variety is superior to both the 'Shawnee' (U.S. Plant Pat. No. 5,686) and 'Choctaw' (U.S. Plant Pat. No. 6,678) varieties. The superior storage ability is due to the increased firmness of the fruit which exceeds that of both the 'Shawnee' (U.S. Plant Pat. No. 5,686) and 'Choctaw' (U.S. Plant Pat. No. 6,678) varieties.

The fresh fruit rates good in flavor, being superior to the 'Shawnee' (U.S. Plant Pat. No. 5,686) variety, but less flavorful than the 'Navaho' (U.S. Plant Pat. No. 6,679) variety. The flavor is sweet and mildly subacid, with a distinct blackberry aroma. Flavor is sweeter and more aromatic than the 'Shawnee' (U.S. Plant Pat. No. 5,686) variety. The soluble solids concentration averages 9.6% which is higher than for the 'Shawnee' (U.S. Plant Pat. No. 5,686) variety. Seed weight averages 3.7 mg/seed (dry wt.), similar to the 'Shawnee' (U.S. Plant Pat. No. 5,686) variety.

Fruit clusters are medium-large, cymose, and are mostly borne on the periphery of the plant canopy, providing easy access to harvest. Flower fertility is high and clusters are well filled.

The new variety has been named the 'Chickasaw' cultivar.

BRIEF DESCRIPTION OF THE PHOTOGRAPHS

The accompanying photographs show typical specimens of the fruit , leaf and canes of the new variety in color as nearly true as it is reasonably possible to make in a color illustration of this character.

DETAILED DESCRIPTION OF THE NEW VARIETY

The following is a detailed description of the botanical and pomological characteristics of the subject blackberry. Color data are presented in Royal Horticultural Society Colour Chart designations and are supplemented with readings from a Minolta Chroma Meter CR-200, version 3.0, which measures absolute chromaticity in tristimulus values Y, x, and y as determined by the Commission Internationale de l'Eclairage (CIE Yxy). Calibration was performed using a standard white plate supplied by the manufacturer.

Where dimensions, sizes, colors and other characteristics are given, it is to be understood that such characteristics are approximations of averages set forth as accurately as practicable.

The descriptions reported herein are from specimens grown at Clarksville, Ark. unless otherwise noted.

Plant:

*Size.*—Large, erect.

*Growth habit.*—Vigorous, prolific suckering from crowns, good suckering from roots, canes erect.

*Growth rate.*—Primocanes reach tipping height (107 cm) 66 days after emergence.

*Productivity.*—High and for duration of almost six weeks; consistent from year to year. Yields consistently range from 7.0 to 7.5 lb/plant, exceeding 'Shawnee' (U.S. Plant Pat. No. 5,686 (with yields of 5 to 7 lb/plant).

*Cold hardiness.*—Hardy to −23° C., similar to 'Shawnee' (U.S. Plant Pat. No. 5,686).

*Canes.*—Thorned, erect. Cane diameter: base 0.98 cm, midpoint 0.93 cm, terminal 0.89 cm. Internode length: base 9.83 cm, midpoint 8.42 cm, terminal 5.56 cm. Thorn Density/30 cm: base 39, midpoint 46, terminal 37. Floricane (winter cane) color: base-Yellow Green Group (146C) Y=26.55, x=0.3609, y=0.4200; midpoint-Yellow Green Group (146C) Y=26.55, x=0.3612, y=0.4225; terminus-Yellow Green Group (146B) Y=10.72, x=0.3582, y=0.3943. Primocane color: base-Yellow Green Group (144A) Y=22.76, x=0.3660, y=0.4714; midpoint-Yellow Green Group (144B) Y=36.23, x=0.3626, y=0.4641; terminus-Yellow Green Group (144B) Y=20.16, x=0.3783, y=0.4297. Date of primocane emergence; Julian 87.

*Disease resistance.*—Moderate to anthracnose; immune to orange rust.

Foliage:

Primocane:

*Leaves.*—Large. Mature compound leaf width 8.57 cm; length 10.47 cm. Leaflet: width 6.4 cm; length 8.7 cm; shape roundish to ovate with subcordate base and acuminate to acute apex; margin serrate; light pubescence on both abaxial and adaxial surfaces. Color: base abaxial-Yellow Green Group (147B) Y=16.44, x=0.3400, y=0.3950; adaxial-Green Group (137A) Y=8.11, x=0.3324, y=0.3983; midpoint abaxial-Yellow Green Group (147B) Y=16.99, x=0.3411, y=0.3955; adaxial-Green Group (137A) Y=7.95, x=0.3326, y=0.3994; terminal abaxial-Yellow Green Group (147B) Y=16.30, x=0.3400, y=0.3948; adaxial-Green Group (137A) Y=8.15, x=0.3329, y=0.3985.

*Petioles.*—Length: 6.5 cm. Color: Yellow Green Group (146B).

*Petioules.*—Length: 2.6 cm. Color: Yellow Green Group 146D).

*Stipules.*—Length: 0.6 cm. Width: 0.1 cm.

Floricane:

*Leaves.*—Large. Mature compound leaf width 9.6 cm; length 7.7 cm. Leaflet: width 2.7 cm; length 5.4 cm; shape ovate, with acute apex and obtuse base; margin serrate; light pubescence on both abaxial and adaxial surfaces. Number of leaflets per compound leaf: 3 occasionally 5. Color: base abaxial-Green Group (137C) Y=12.97, x=0.3380, y=0.3925; adaxial Green Group (137B) Y=8.51, x=0.3335, y=0.3949; midpoint abaxial Green Group (137C) Y=14.85, x=0.3409, y=0.3945; adaxial-Green Group (137B) Y=7.45, x=0.3328, y=0.3904; terminal adaxial-Green Group (137C) Y=14.52, x=0.3419, y=0.3953; adaxial-Green Group (137B) Y=7.61, x=0.3343, y=0.3932.

*Petioles.*—Length: 2.3 cm. Color: yellow Green Group (146A).

*Petioules.*—Length: 0.6 cm. Color: Yellow Green Group (146B).

*Stipules.*—Length: 0.8 cm. Width: 0.1 cm.

Flowers:

*Date of bloom.*—First — Julian 104; 50% — Julian 122; Last — Julian 150.

*Blossom color.*—White Group (155C) Y=74.82, x=0.3211, y=0.3267.

*Reproductive organs.*—Stamens — erect, numerous. Pistils — numerous. Pollen — normal and abundant.

*Flower diameter.*—3.5 cm.

*Petal size.*—Length: 1.5 cm. Width: 1.3 cm.

*Number flowers per cluster.*—5.

*Number of petals per flower.*—5.

*Number of sepals per flower.*—5.

*Peduncle length.*—2.6 cm.

*Peduncle color.*—Yellow Green Group (144A).

*Cyme type.*—Elongate simple cyme.

Fruit:

*Maturity.*—Late, 3 days after 'Shawnee' (U.S. Plant Pat. No. 5,686). Average first ripe date is June 10. Average period of ripening is June 10 to July 20.

*Size.*—Very large, average 10.7 g, uniform. Diameter: Fruit at primary position on inflorescence: equator 2.6 cm, base pole 2.7 cm, terminal pole 2.4 cm; secondary fruit equator 2.5 cm., base pole 2.4 cm, terminal pole 2.2 cm. Length (Primary fruit) 3.08 cm.

*Shape.*—Long, cylindrical, and slightly flattened, uniform.

*Color.*—Glossy black; Black Group (202A) Y=3.06, x=0.3134, y=0.3152.

*Drupelet size.*—Medium, 0.54 cm.

*Seed size.*—Medium, 3.7 mg (dry wt.).

*Soluble solids.*—9.6%.

*pH.*—3.25 (as measured by a by pH meter on undiluted juice from a sample of 25 fully-ripe berries).

*Acidity.*—1.41 g tartaric acid/100 ml.

*Uses.*—Fresh and processed, jellies, jams, juice, wine.

The variety: The most distinctive features of the variety are its very large fruit size, late ripening, high fruit yields, erect canes, long fruiting season, and good postharvest fruit characteristics.

We claim:

1. A new and distinct variety of blackberry plant, substantially as illustrated and described, characterized by its very large fruit size, erect canes, late ripening, high fruit yields, long harvest period, and good postharvest fruit quality.

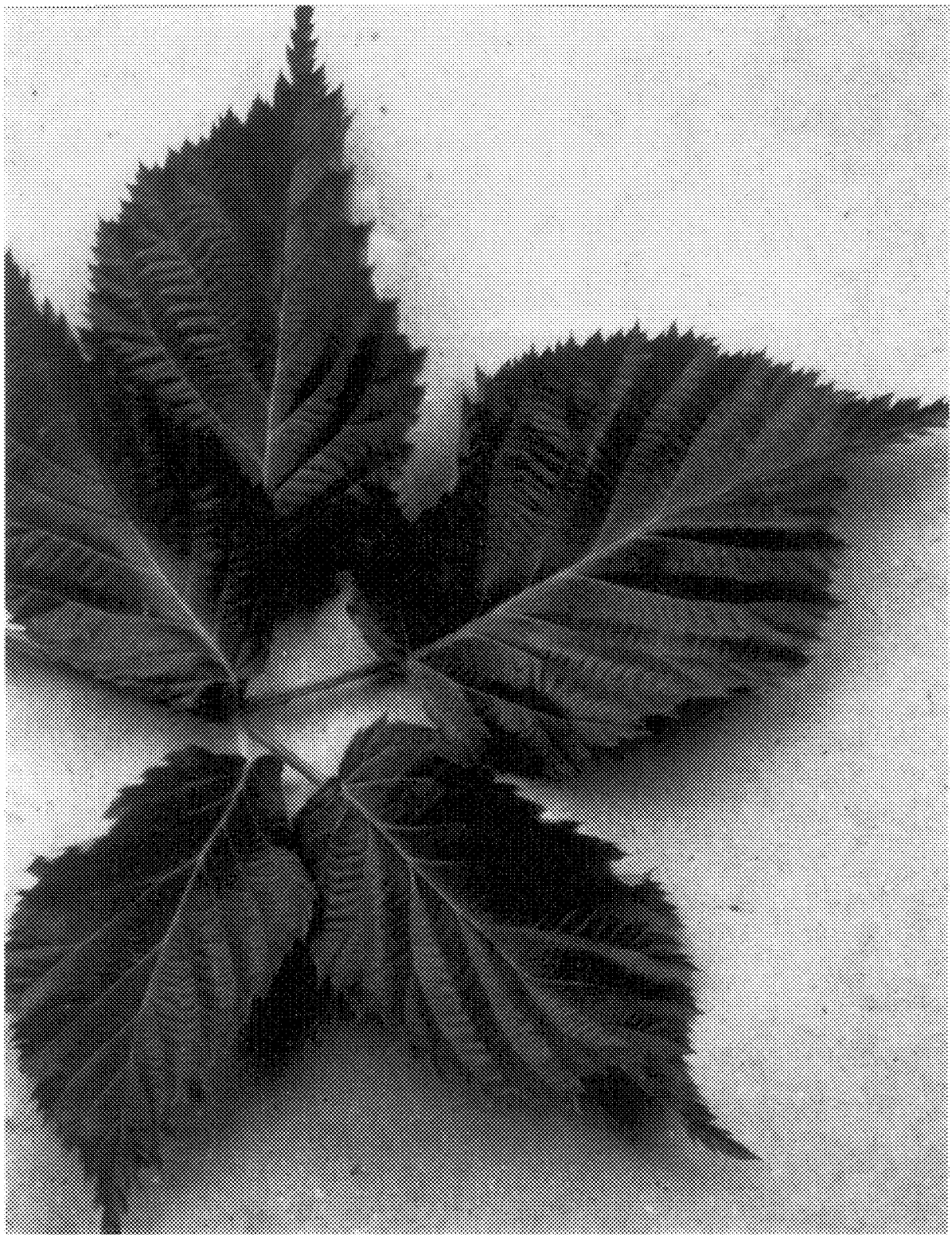

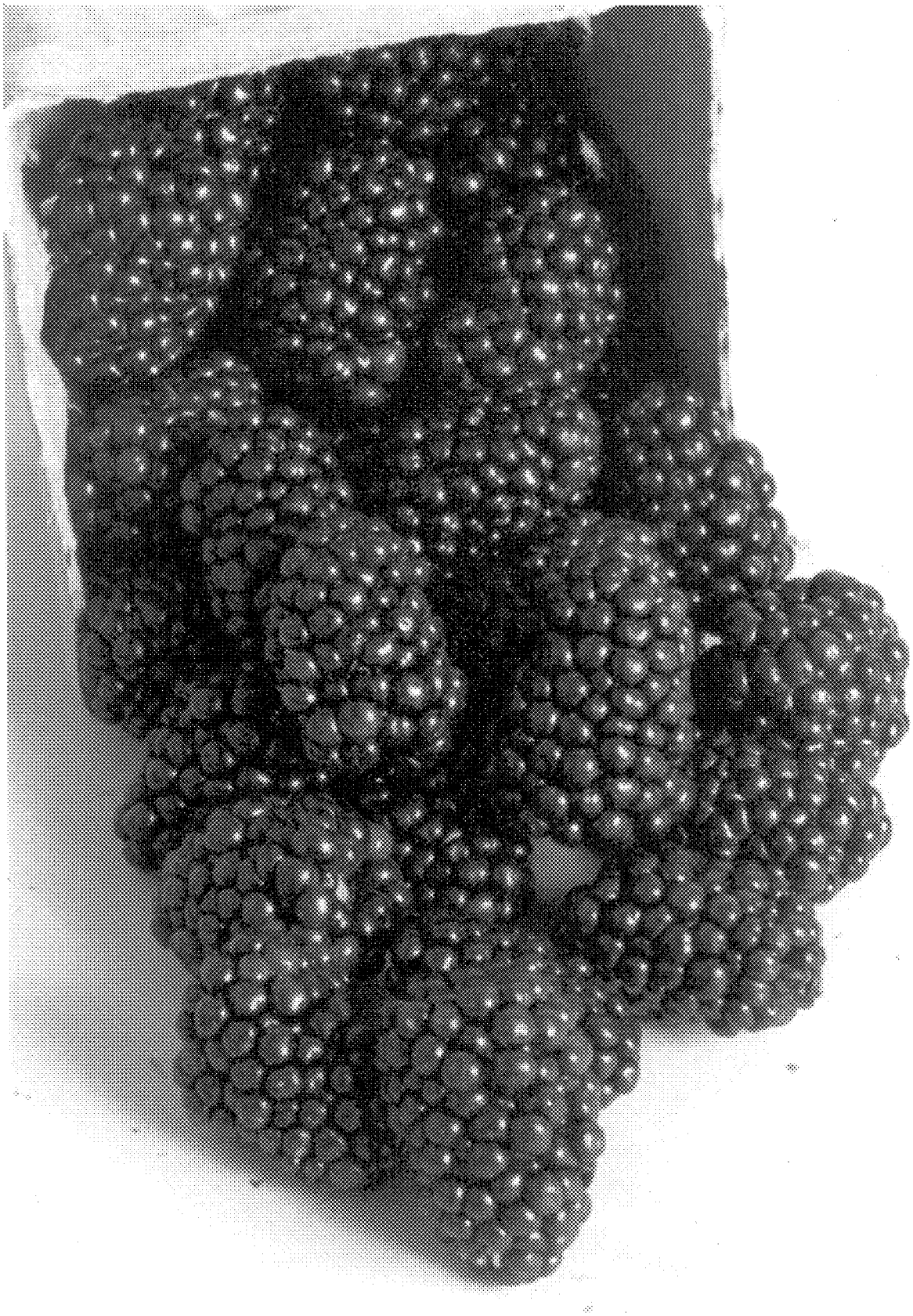

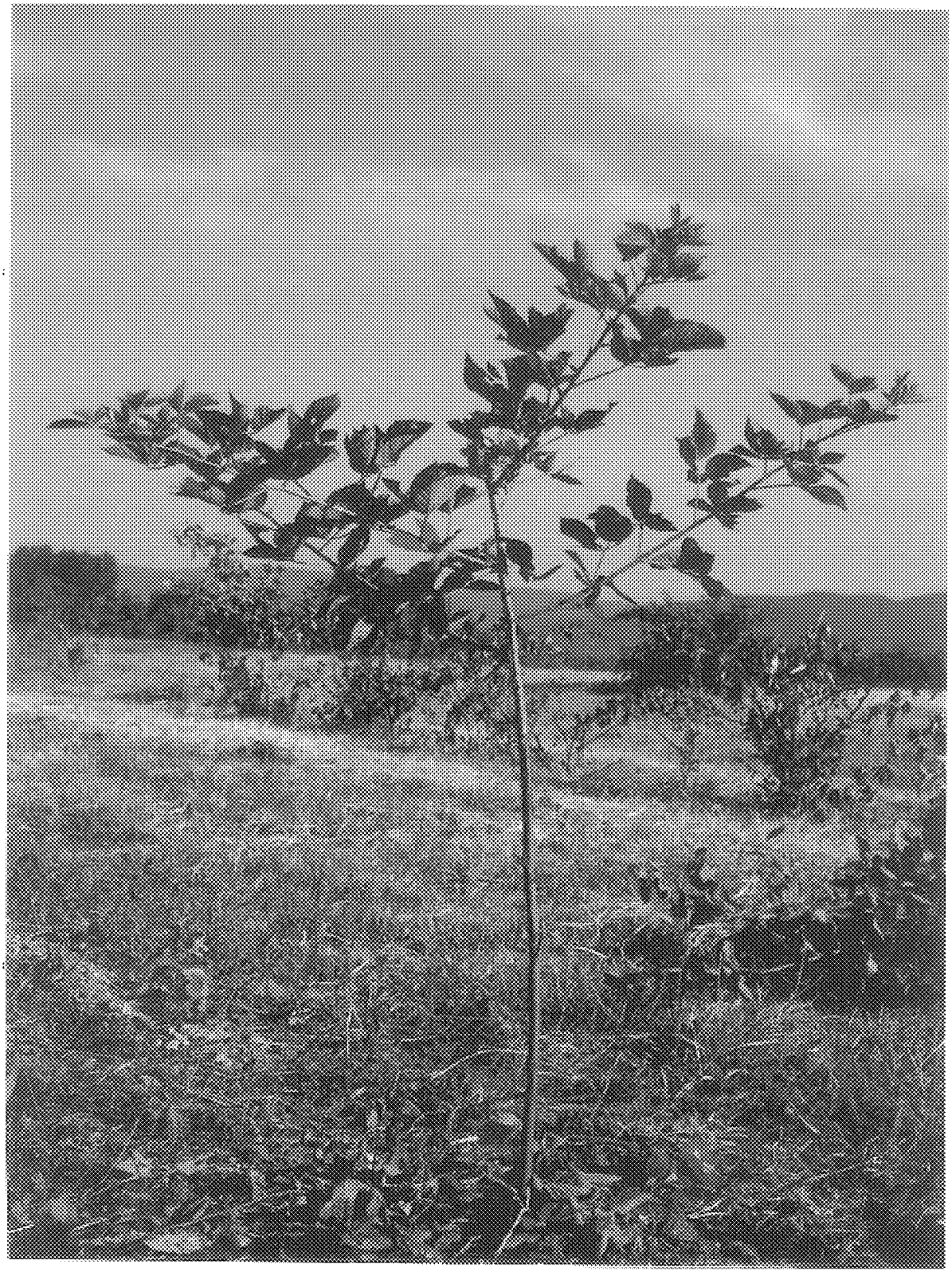

* * * * *